United States Patent [19]

Gilman

[11] Patent Number: 5,318,502

[45] Date of Patent: *Jun. 7, 1994

[54] HEARING AID HAVING GEL OR PASTE TRANSMISSION MEANS COMMUNCATIVE WITH THE COCHLEA AND METHOD OF USE THEREOF

[76] Inventor: Samuel Gilman, 11920 Dorothy St., Los Angeles, Calif. 90049

[*] Notice: The portion of the term of this patent subsequent to Jan. 5, 2010 has been disclaimed.

[21] Appl. No.: 781,833

[22] Filed: Oct. 24, 1991

Related U.S. Application Data

[63] Continuation-in-part of Ser. No. 599,066, Oct. 17, 1990, Pat. No. 5,176,620.

[51] Int. Cl.⁵ .......................................... H04R 25/00
[52] U.S. Cl. .................................................. 600/25
[58] Field of Search ......................... 128/420.6; 600/25

[56] References Cited

U.S. PATENT DOCUMENTS

| | | | |
|---|---|---|---|
| 4,606,329 | 8/1986 | Hough | 600/25 |
| 4,844,080 | 7/1989 | Frass et al. | 128/660.01 |
| 5,176,620 | 1/1993 | Gilman | 600/25 |

Primary Examiner—William E. Kamm
Assistant Examiner—Scott Getzow
Attorney, Agent, or Firm—Albert O. Cota

[57] ABSTRACT

A hearing aid (100) is provided for surgically implanting in the ear of a subject. A gel or paste filled tube (142) is positioned between an orifice of the cochlea and a subcutaneous amplifier (200). A microphone (122) converts sound waves outside the subject into electrical signals which are amplified by the amplifier and are converted back into amplified mechanical motion by a transducer means (124). The amplified mechanical motion is transmitted through the tube by the gel or paste to the cochlea bypassing the outer and middle ears. The gel or paste and dimensions of the tube are selected to substantially match the acoustic impedance of the cochlea at the distal end of the tube.

48 Claims, 5 Drawing Sheets

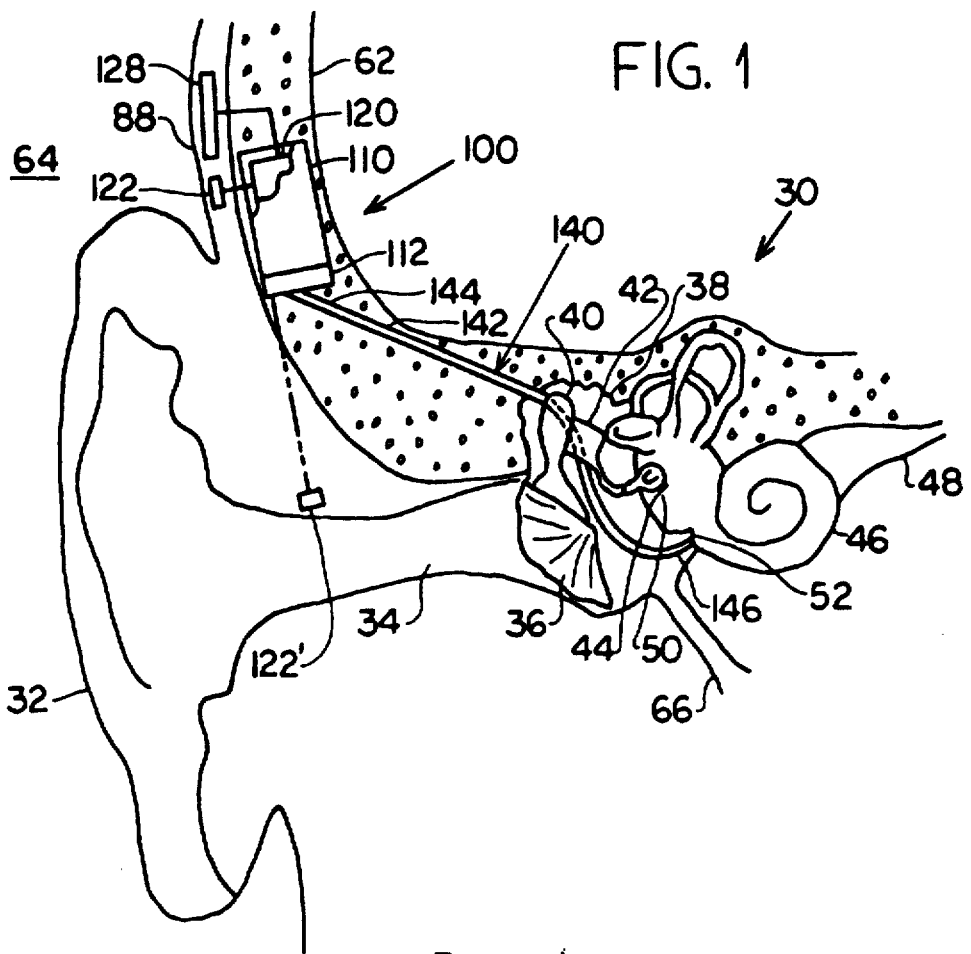
FIG. 1
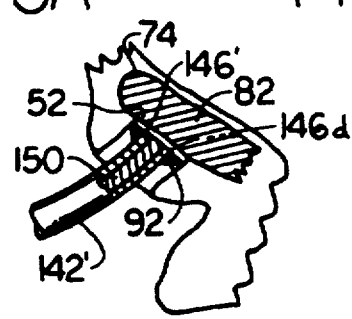
FIG. 3A
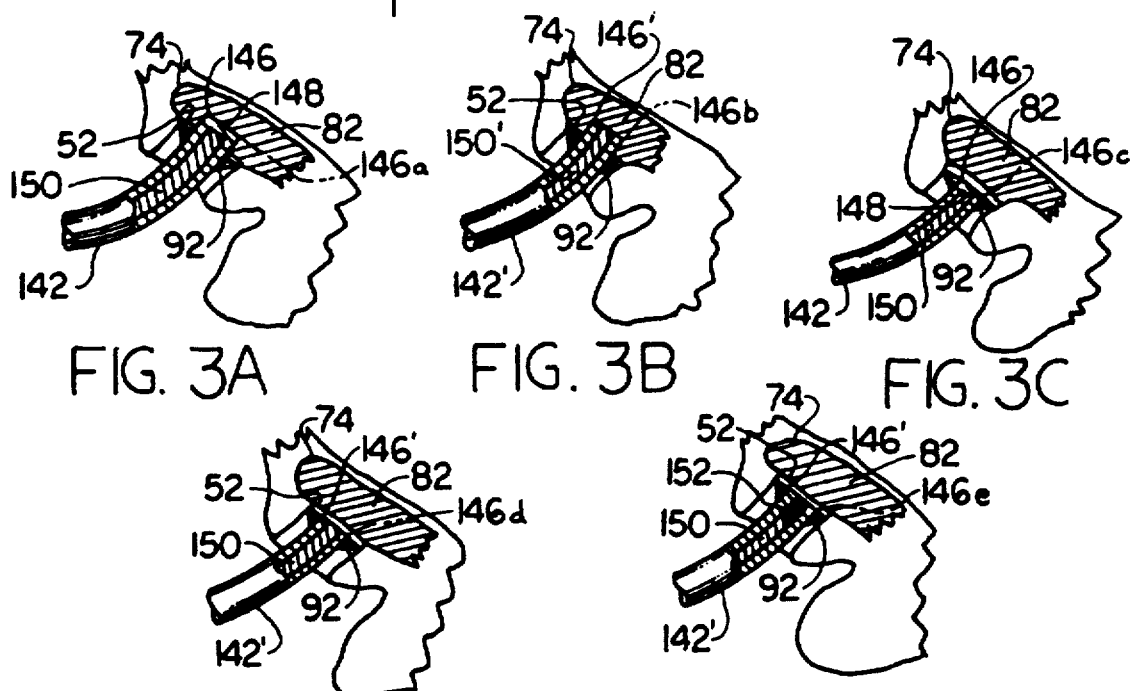
FIG. 3B
FIG. 3C
FIG. 3D
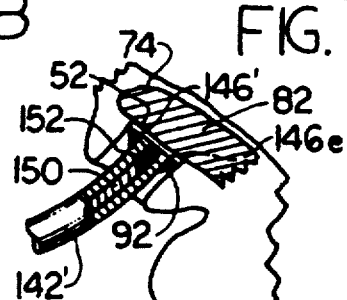
FIG. 3E

HEARING AID HAVING GEL OR PASTE TRANSMISSION MEANS COMMUNCATIVE WITH THE COCHLEA AND METHOD OF USE THEREOF

CROSS REFERENCE TO RELATED APPLICATION

This application is a continuation-in-part of U.S. patent application Ser. No. 07/599,066 filed Oct. 17, 1990, and issued on Jan. 5, 1993 as U.S. Pat. No. 5,176,620.

TECHNICAL FIELD

The present invention pertains to hearing aids, and more particularly to hearing aids utilizing a gel or paste transmission means.

BACKGROUND ART

The ear directs, amplifies, and converts sound waves into nerve impulses which are interpreted by the brain. The outer ear or pinna directs the sound waves into the auditory canal terminating at the eardrum or tympanic membrane. Attached to the tympanic membrane on the other side is the malleus, the first of three small bones in the middle ear called the ossicles. The other ossicles are the incus and the stapes. When the eardrum moves in response to the sound waves, the malleus articulates with the incus which in turn articulates with the stapes thereby transmitting the mechanical movement of the eardrum through the middle ear. In addition, the ossicles amplify the mechanical movement by their leveraged relationships. The foot plate of the stapes is attached to a covered resilient oval window in the fluid filled inner ear or cochlea. As the oval window moves in response to the mechanical movement of the stapes, pressure waves are transmitted into the liquid filled cochlea which transduces the pressure waves into electrical signals that in turn are sensed by nerves inside the cochlea. In addition to transmitting the mechanical movement, the oval window amplifies the pressure of the wave appearing at the eardrum because its area is smaller than that of the eardrum. In a normal ear, the mechanical advantage of the ossicles, together with the ratio of the oval window area to the eardrum area, provides a 20 times gain in sound pressure delivered to the cochlea.

Two broad categories of hearing loss are conduction loss and sensorineural (nerve) hearing loss. Conduction hearing loss refers to problems in the conduction of sound from the eardrum to the cochlea while sensorineural loss refers to losses due to defects in the cochlea, the cochlear nerves or the auditory centers of the brain. Measures to alleviate hearing deterioration vary depending on the part of the hearing system that is involved. Apparatus has been designed to amplify acoustical energy and apply it either through its normal path or by vibrating some part of the ossicles. Examples of the former have been available for years. Examples of the latter include implanted magnetic materials, coils, and piezo-electric materials in contact with the ossicles. A third type of apparatus stimulates the cochlear nerves electrically but has a significant disadvantage by requiring the user to relearn the significance of the signals received. A detailed survey of these types of devices is given in U.S. Pat. No. 4,850,962 to Schaefer. For example, U.S. Pat. No. 3,882,285 to Nunley et al. shows an implant taking sound energy from the auditory canal and stimulating the ossicular chain via a direct mechanical link. U.S. Pat. No. 4,606,329 to Hough uses magnetic coupling through the skin to a coil implanted in the skull. This coil feeds signals in turn to a coil embedded near the middle ear cavity which induces mechanical motion in magnetic material attached to some part of the ossicular chain. In U.S. Pat. Nos. 4,850,962 and 4,729,366 to Schaefer, one of the ossicular bones is removed and mechanical vibration of the tympanic membrane is converted, in an implant, to an electrical signal by a transducer mounted proximate to the terminated ossicular chain. The electrical signals are then applied across the interrupted chain to the promontory of the cochlea or through a hole in the oval window or converted into mechanical motion which is transmitted to the stapes. Other devices are shown in U.S. Pat. Nos. 3,870,832 to Fredrickson; U.S. Pat. No. 4,052,754 to Homsy; U.S. Pat. No. 4,063,048 to Kissiah; U.S. Pat. No. 4,357,497 to Hochmair et al.; and U.S. Pat. No. 4,696,287 to Hortmann. Publications of background interest are Hough J. et al. "Experiences with implantable hearing devices and a presentation of a new device" *Anno Otol Rhinol Laryngol* 95: 1986 60–65, Suzuki J. et al. "Middle ear implant for humans." *Acta Otolaryngol* 1985:99 313–317, and Hough J. et al. "A middle ear implantable hearing device for controlled amplication of sound in the human: a preliminary report" *Laryngoscope* 97: Feb. 1987, 141–151.

A fourth type of device produces amplified sound waves in the middle ear. In U.S. Pat. No. 3,346,704 to Mahoney, such a device is described in which a sound receiving and amplifying unit is implanted in the mastoid antrum with a "microphone tube" beginning at a point just under the skin inside the ear canal and a "speaker tube" extending from a speaker into the middle ear space. However, Mahoney has a significant disadvantage in that when acoustical energy from the air is applied directly to the oval window instead of being conducted from the eardrum through the ossicles, the sound transfer is very much reduced because of the greater acoustic impedance of the liquid-filled cochlea compared to that of air. The impedance matching effect provided by the mechanical advantage of the ossicles, together with the ratio of the oval window area to the eardrum area, is lost if the sound energy is introduced directly into the middle ear space.

U.S. Pat. No. 4,988,333 to Engebretson et al. discloses an air filled chamber with a diaphragm attached to the malleus and having an air filled tube leading to an electro-acoustic transducer and amplifier. A similar air filled tube leads from a receiver powered by the amplifier to a similar air filled chamber with a diaphragm attached to the stapes. Alternatively, the electrical signals from the amplifier may go directly to a cochlear implant.

DISCLOSURE OF INVENTION

The present invention is directed to a gel or paste transmission means for transmitting acoustical energy to the cochlea. In a preferred embodiment, the gel or paste transmission means is a gel or paste filled tube which is surgically inserted through the middle ear to an orifice in the cochlea. The gel or paste filled tube acts as a transmission line with little losses because the gel or paste can be adjusted to have compatible acoustic properties to the perilymph in the cochlea and the impedance of the transmission line can be more closely matched to the acoustic impedance of the cochlea at the termination of the tube at the cochlea.

In accordance with one important aspect of the invention, an electro-mechanical means is provided that converts acoustical energy processed through microphone, amplifier, and transducer means to mechanical motion for application to the gel or paste transmission means. In a preferred embodiment, the electro-mechanical means is housed in a biologically inert material such as titanium and is implanted with the microphone means subcutaneously behind the ear or near the auditory canal.

In accordance with another important aspect of the invention, a method is provided for improving the hearing of a hearing impaired subject comprising the steps of placing a gel or paste transmission means from a proximal end to a distal end in operative association with an orifice of the cochlea, converting sound energy to mechanical motion, and applying the mechanical motion to the proximal end of the transmission means.

The novel features of the invention are set forth with particularity in the appended claims. The invention will be best understood from the following description when read in conjunction with the accompanying drawings.

BRIEF DESCRIPTION OF DRAWINGS

FIG. 1 is a sectional elevation view of the human hearing system illustrating an implanted hearing aid in accordance with an embodiment of the present invention;

MODES FOR CARRYING OUT THE INVENTION

Figure 2:
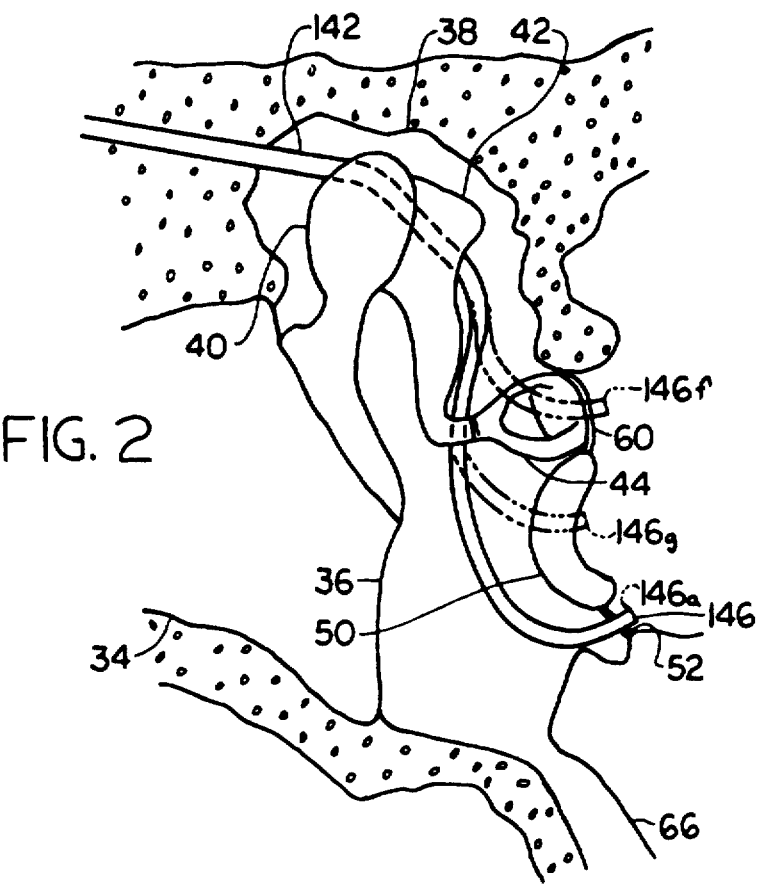
FIG. 2 is an enlarged sectional view of the middle ear cavity showing several positions of the gel or paste transmission means of the present invention.

An embodiment, in accordance with the present invention, of a hearing aid 100 is illustrated in FIG. 1 in operative association with the hearing systems 30. The enclosure 110 is implanted in the mastoid bone 62. A gel or paste transmission means 140 in the form of a gel or paste filled tube 142 is also implanted in the mastoid bone 62. The proximal end 144 of the gel or paste filled tube 142 connects through a coupler 112 to the enclosure 110 while the distal end 146 is inserted through the middle ear cavity 38 to the round window 52 of the cochlea 46. Electro-mechanical means 120 housed in the enclosure 110 converts acoustical energy received by microphone means 122 from the outer environment 64 via skin flap 88 into mechanical motion which is transmitted by the gel or paste filled tube 142. An alternate position 122' for the microphone adjacent the auditory canal 34 may also be used. An induction coil 128 is mounted under the skin flap 88 for receiving magnetic energy from an external source for recharging the battery (shown in FIG. 4) of the electro-mechanical means 120.

The hearing system 30 includes the outer ear 32; the auditory canal 34; the eardrum or tympanic membrane 36; the ossicular chain made up of malleus 40, the incus 42, and the stapes 44; the cochlea 46; and the cochlear nerve 48. Also illustrated is the eustacian tube 66 which equalizes pressures in the middle ear to that in the environment. In a normal ear, acoustical energy reaches the eardrum through the outer ear and the auditory canal where it causes the eardrum to vibrate. These vibrations are transmitted through the ossicular chain to the cochlea where they are converted into nerve impulses which are sent to the brain through the cochlear nerve. The present invention bypasses conduction hearing loss problems by going directly to the cochlea.

The features of this invention distinguish it from previous approaches to implantable hearing aids. These features involve the acoustics of transmitting sound directly into the cochlea and in particular the use of tubes for transmitting such sound through different media contained in the tubes including gels and pastes.

A part of this invention is the selection of gels or pastes which are acoustically and biologically compatible with the liquid (perilymph) in the scala vestibuli or scala tympani of the human cochlea (inner ear) either by direct contact or acoustically. Such gels or pastes have acoustic characteristics selected to maximize the conduction of sound into the cochlea.

A gel is an elastic coherent mass consisting of a liquid in which ultramicroscopic particles are dispersed or arranged in a fine network extending through the mass. The particles may be, for example, large molecules, such as proteins or small crystals such as bentonite, or polymer particles such as styrene. The rheological properties of a gel vary between those of a viscous or elastic liquid and those of a solid. Examples are:

Agar Colloidal Ferric Hydroxide gel, silicone gel, such as Q7-2218 silicone gel and the like.

A paste is a semi-solid preparation of a fatty, viscous or mucilagenous base containing one or more powdered solid materials as a mixture. The base may be viscous petroleum products, animal or vegetable fats, synthetic materials such as silicone or other materials providing a semi-rigid structure which can be readily formed but which will not readily flow. Examples are:

a mixture of powdered silicon dioxide in silicone liquid, modeling clay, putty, toothpastes, rubbing compounds and the like.

The advantages of the gel or paste filled tube of the present invention in comparison to the air filled tubes of the prior art can be made on the basis of viscous losses in the medium, losses due to impedance mismatches during transmission, and losses due to impedance mismatches during the transfer of sound into the cochlea. Losses due to viscous friction are significantly greater in a tube containing air at room temperature than in a gel or paste in the same tube even though the kinematic coefficient of viscosity of the gel or paste may be considerably greater than the corresponding viscosity of air. These losses are proportional to a function of both frequency and the bore of the tube and are substantially less in a gel or paste filled tube compared to a significant loss in air. (See *Fundamenral of Acoustics*, by Kinsler & Frey, John Wiley & Sons, ©1962).

Impedance mismatch such as when going from one bore size to another or when going from one medium to another create losses due to reflections of sound from the impedance transition. For example, sound going from a 2 millimeter bore air filled tube into the air space of the middle ear can suffer a reduction in sound energy level of about 88% so that only about 12% of the incoming sound is available for use (*Fundamentals*, supra, pp. 131-133). Similarly, the transfer of the sound in the air of the middle ear to the cochlea via the oval (or round) window suffers a further decline. For the average ear, the reduction in sound is approximately 20:1 so that only 5% of the sound pressure is transmitted to the cochlea. Combining the loss due to going from the air tube into the middle ear and going from the air in the middle ear to the input to the cochlea can result in less than 1% of the sound generated by the output transducer of the hearing aid going into the cochlea.

In contrast to this, the gel or paste filled tube of the present invention whose acoustic impedance has been matched to that of perilymph suffers substantially no loss if the bore of the tube is the same as that of the cochlea at the operative intersection of the end of the tube with the cochlea. Further, the loss is only 36% if the bore of the tube is one-half the bore of the cochlea at the operative intersection. Thus as much as 64% of the sound energy created by the output transducer of the present invention is transmitted into the cochlea even when the bore of the tube is only one-half that of the cochlea at the operative intersection.

Another problem with introducing amplified sound into the middle ear space through a tube is the opposing operation of the oval and round windows of the cochlea. When the sound waves are transmitted to the oval window by the stapes as occurs in a normal ear, the round window moves in the opposite direction. However, when amplified sound is directed into the middle ear space, the motion of the two windows oppose each other instead of moving cooperatively. This can result in a further loss in sound power transmitted into the cochlea.

FIG. 2 is an enlarged sectional view of the middle ear cavity 38 illustrating the distal end 146 of the gel or paste filled tube 142 of the present invention led around the malleus 40 and the incus 42 and surgically inserted through the membrane covered round window 52 to the position 146a. Alternatively, the distal end 146 may be surgically inserted through the stapes 44 and oval window 60 to the position 146f. Or the distal end 146 may be surgically inserted by a fenestration through the promontory 50 to the position 146q, or through the vestibule. The tube 142 may be of a biologically inert material such as implant grade silicone elastomer sold under the trademark Silastic by Dow Corning Corporation or under the trademark Tygon by Norton Performance Plastics.

FIGS. 3A, B, C, D, and E show various terminations of the gel or paste filled tube 142, 142' with the round window 52 and the perilymph 82 of the scala tympani 72. In FIG. 3A the distal end 146 penetrates the round window 52 placing the membrane 148 in contact with the perilymph 82 in position 146a. The membrane 148 closes the distal end 146 of the tube 142 which is filled with a gel or paste 150. Because the impedance of the gel or paste 150 is selected to substantially match the impedance of the perilymph 82, virtually no sound pressure is lost at the membrane 148. The tube 142 is held in place with a biologically compatible sealing material 92 well known to the art such as Gelfoam sold by Upjohn, cartilage, perichondrium, mucosal seal, blood clot, fat and (for silicon tubing) Silastic 7-2947 by Dow Corning. Alternatively, the tube 142 may be surrounded by materials such as titanium or synthetic bone which are capable of being bonded by natural bone.

FIG. 3B is similar to FIG. 3A except the tube 142' has an open distal end 146', placed in position 146b. The gel or paste 150' filling the tube 142' is selected to be compatible with the perilymph 82 and not to migrate substantially into the perilymph over time. The gel or paste 150' can either be of a uniform consistency throughout the tube if it is suitably compatible with the perilymph and does not migrate or the gel or paste at the distal end can be further treated or cured to make it more compatible with the perilymph and less likely to migrate. For example, the Dow Corning Silicon Gel can be made stiffer at the end by increasing the amount of its B component at the end in comparison to its A component. FIG. 3C shows the distal end 146 of the gel or paste filled tube 142 placed against the round window 52 in position 146c. The membrane 148 abuts the round window 52. Because the impedance of the gel or paste 150 is selected to substantially match the impedance of the perilymph 82 as is the case in FIG. 3A, virtually no sound pressure is lost due to the membranes 148 and 52. FIG. 3D is similar to FIG. 3C except the tube 142' has an open distal end 146' placed in position 146d abutting the round window 52. Finally, FIG. 3E is similar to FIG. 3D except the distal end 146' of the gel or paste filled tube 142' is filled with a seal 152.

Figure 3F:
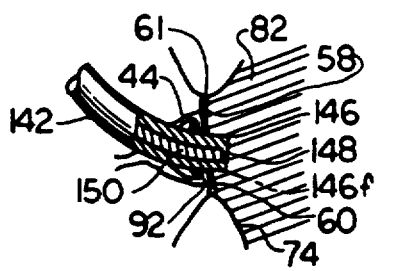
FIGS. 3F, G, H, I, and J are sectional views illustrating various terminations of the gel or paste transmission means with respect to the oval window.
Figure 3G:
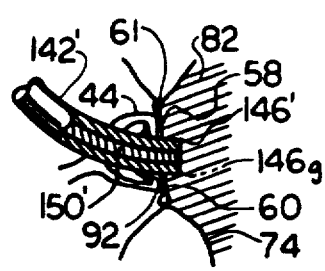
FIGS. 3A, B, C, D, and E are sectional views illustrating various terminations of the gel or paste transmission means with respect to the round window.
FIGS. 3K, L, M, N, and P are sectional views illustrating various terminations of the gel or paste transmission means with respect to the oval window after the stapes is removed.
FIGS. 3Q, R, S, T, and U are sectional views illustrating various terminations of the gel or paste transmission means with respect to an aperture opened by surgical fenestration in the vestibule or promontory.
Figure 3H:
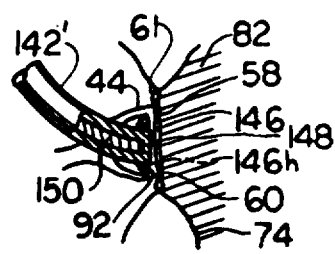
Figure 3I:
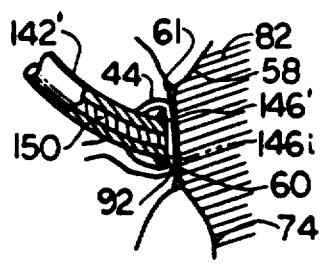
Figure 3J:
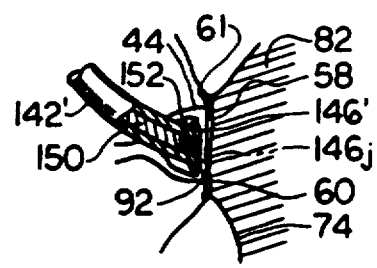

FIGS. 3F, G, H, I, and J illustrate various terminations of the gel or paste filled tube 142, 142' with the stapes footplate 58, the oval window 60, and the perilymph 82 of the scala vestibuli 74. These figures indicate the distal end embodiments 146, 146' in positions 146f, 146g, 146h, 146i, and 146j which are similar to positions 146a, 146b, 146c, 146d, and 146e of FIGS. 3A, B, C, D, and E with the stapes footplate 58 and the oval window 60 replacing the round window 52.

Figure 3K:
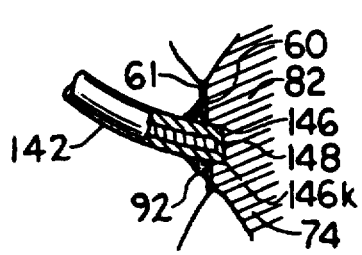
Figure 3L:
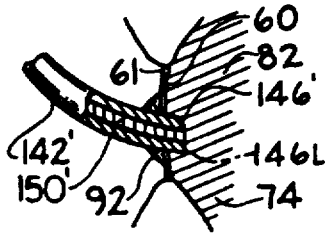
Figure 3M:
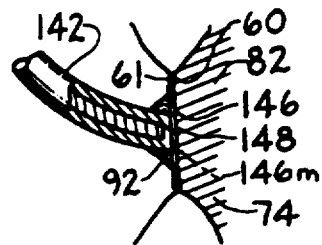
Figure 3N:
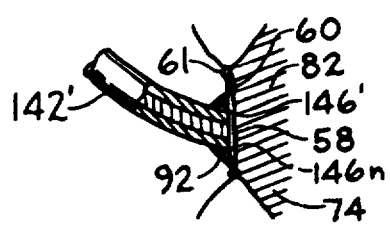
Figure 3P:
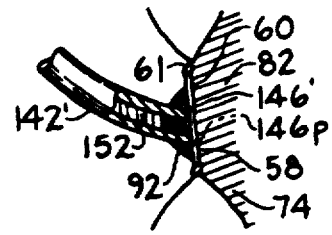

FIGS. 3K, L, M, N, and P illustrate various terminations of the gel or paste filled tube 142, 142' with the oval window 60 and the perilymph 82 of the scala vestibuli 74 after the stapes has been surgically removed. The figures indicate the distal end 146, 146' in positions 146k, 146l, 146m, 146n, and 146p which are similar to position 146f, 146g, 146h, 146i, and 146j of FIGS. 3F, G, H, I, and J with the stapes 44 removed.

Figure 3Q:
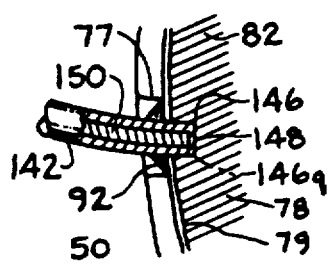
Figure 3R:
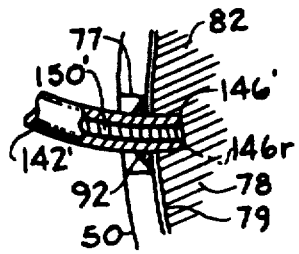
Figure 3S:
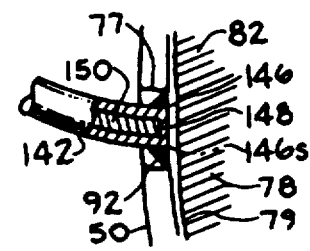
Figure 3T:
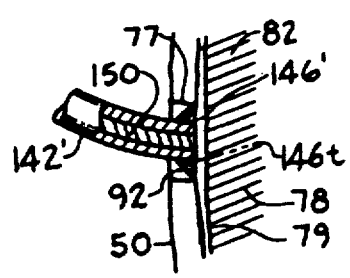
Figure 3U:
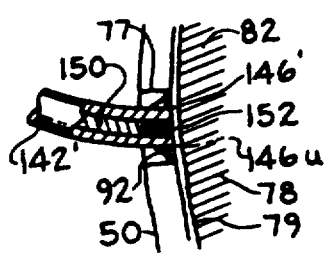

FIGS. 3Q, R, S, T, and U illustrate termination of the gel or paste filled tube 142, 142' with the perilymph 82 through an aperture 77 in the vestibule or promontory 78. The aperture is opened in the cochlea by surgical fenestration. The figures indicate the distal end embodiments 146, 146' in positions 146q, 146r, 146s, 146t, and 146u which are similar to 146a, 146b, 146c, 146d, and 146e of FIGS. 3A, B, C, D, and E with the lining 79 replacing the round window 52.

Figure 4:
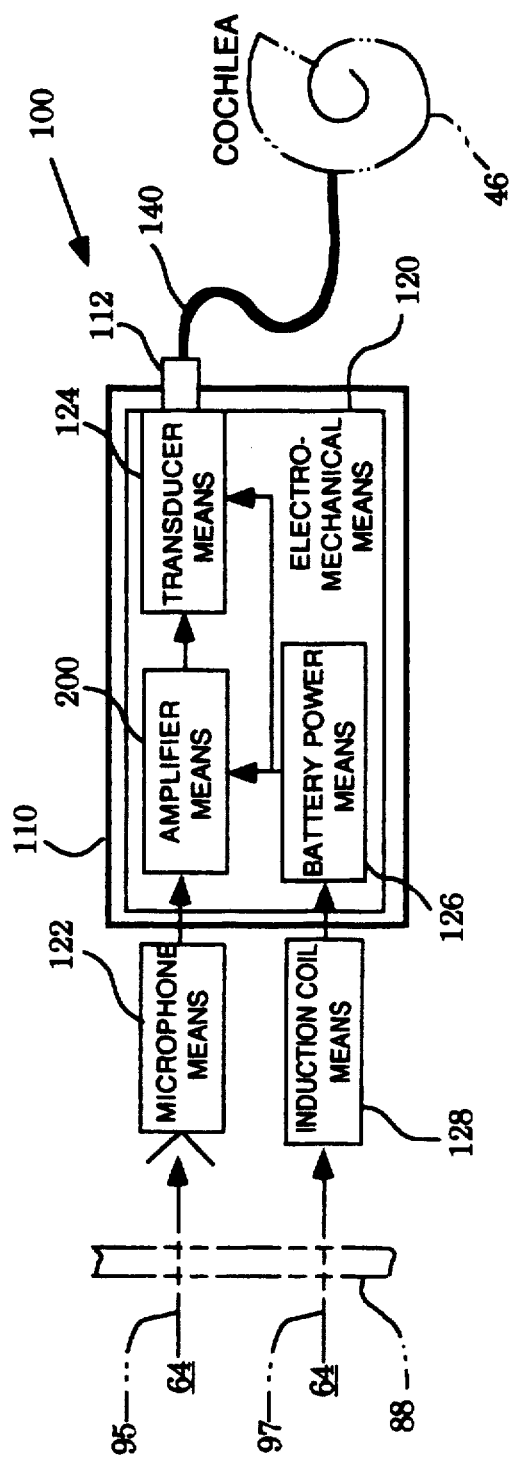
FIG. 4 is a block diagram of an embodiment of the present invention.

FIG. 4 is a block diagram of an embodiment of the present invention. Acoustical energy is imparted to the cochlea 46 via the gel or paste transmission means 140 by the electro-mechanical means 120. Acoustical energy represented by the arrow 95 from the outer environment 64 passes through the skin flap 88 and is converted by the microphone 122 to electrical signals which are amplified by the amplifier 200 and transformed to mechanical motion by the transducer 124 which may be immersed in the same or similar gel or paste as in the tube 140. The coupler 112 allows the engagement and disengagement of the transducer 124 to the gel or paste transmission means 140 when the electro-mechanical means is removed for servicing. Power is supplied by the battery power means 126 which can be recharged by currents induced by magnetic fields represented by arrow 97 into the induction coil means 128 through the skin flap 88. The electro-mechanical means 120 is mounted in the enclosure 110 which may be of a biologically inert material such as titanium.

The transducer means 124 may be any of those well known in the art including the constant displacement type where the displacement is proportional to the applied voltage. Examples are piezo-electric, magnetostrictive and capacitive transducers. The microphone means 122, induction coil means 128, and the battery power means 126 may be any of those well known in the art.

Figure 5:
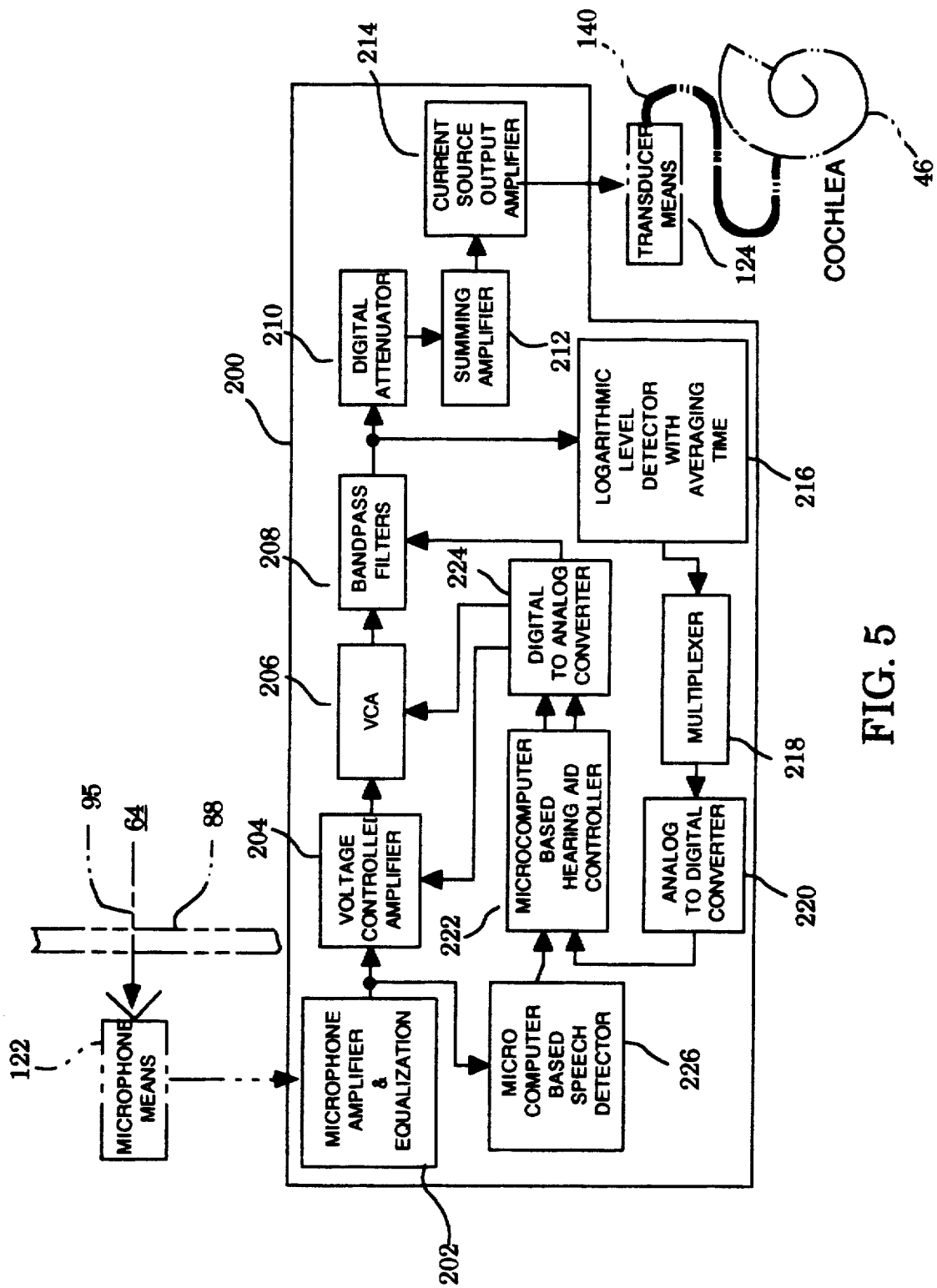
FIG. 5 is a block diagram of an embodiment of the amplifier means of the present invention.

FIG. 5 is a block diagram of the amplifier means 200. Input signals from the microphone 122 are amplified by a microphone amplifier and equalization circuit 202 and then go to a processor 222 controlled VCA (voltage controlled amplifier) 204. The signal is then split up into two or more frequency bands each of which has a voltage controlled amplifier 206 at its input. This provides control of the frequency spectrum from control signals obtained from the processor 222. The output from each band 208 can h=preset from the band attenuator 210. The output from each band is then summed in summing amplifier 212 and goes to the current source output amplifier 214 providing the electrical signal to the output transducer 124.

In a completely separate circuit, the signal level of each band is sequentially averaged through logarithmic detector 216, the value of the average is determined, and the result is converted to a digital signal which can then be compared to the previously stored reference value for that band. The microprocessor 222 then adjusts the voltage applied to each band voltage control amplifier so as to achieve at all times the level for that band that has been preset into the microprocessor 222.

The overall input level is measured in another circuit having a speech detector 226. When the preset algorithm determines that speech is not present, the hearing aid is put in standby mode to reduce noise and save battery power.

Many of the features of the amplifier means 200 including the ability to a) control amplification in accordance with a set of predetermined instructions; b) reduce noise by selected frequency band limiting; and c) conserve operating power using speech detection means to activate the hearing aid were disclosed by the present inventor in U.S. Pat. No. 4,596,902.

Thus it may be seen that a hearing aid has been provided having gel or paste transmission means for substantially matching the impedance of orifices of the cochlea so as to transmit acoustical energy thereto. The gel or paste transmission means is a gel or paste filled tube which is placed in operative contact with the cochlea.

Although the present invention has been described with reference to preferred embodiments, numerous modifications and rearrangements can be made with the equivalent result still embraced within the scope of the invention.

What is claimed is:

1. An acoustical transmission means for transmission of acoustical energy to the cochlea, comprising:
   gel or paste conduction means for conducting acoustical energy therealong, and
   impedance matching means, terminating said gel or paste conduction means and adapted to be disposed in direct operative association with a window or aperture in the cochlea for introducing said acoustical energy therthrough.

2. An acoustical transmission means as defined in claim 1 wherein said gel or paste conduction means comprises:
   a tube having a bore therethrough; and
   a gel or paste filling said bore.

3. An acoustical transmission means as defined in claim 2 wherein aid gel or paste has equivalent acoustical characteristics as the perilymph.

4. An acoustical transmission means as defined in claim 2 wherein the characteristics of said gel or paste allow said gel or paste to maintain its form substantially over time.

5. An acoustical transmission means as defined in claim 2 wherein said gel is silicone gel.

6. An acoustical transmission means as defined in claim 2 wherein said paste is a mixture of powdered silicon dioxide in silicone liquid.

7. An acoustical transmission means as defined in claim 2 wherein said impedance matching means comprises:
   a tube end defined by said tube wherein said bore therein is substantially circular and has a diameter being adapted to abut with substantially one-half the diameter of said window or aperture which said tube end is disposed at an operative intersection therewith; and
   means for sealing said intersection.

8. An acoustical transmission means as defined in claim 2 wherein said impedance matching means comprises:
   a tube end defined by said tube wherein said bore therein is substantially circular and has a diameter being adapted to abut with an area substantially greater than one-half the diameter of said window or aperture which said tube end is disposed at an operative intersection therewith; and
   means for sealing said intersection.

9. An acoustical transmission means as defined in claim 8 wherein said impedance matching means further comprises a membrane defined by said tube across said tube end.

10. An acoustical transmission means as defined in claim 8 wherein said sealing means comprises a sealing material arranged to seal said intersection.

11. An acoustical transmission means as defined in claim 10 wherein said sealing material comprises Silastic 7-2947.

12. An acoustical transmission means as defined in claim 10 wherein said window or aperture is the round window of the cochlea, said tube end being adapted to abut said round window, and said sealing material is arranged to conform with said tube end and said round window to seal said intersection therebetween.

13. An acoustical transmission means as defined in claim 10 wherein said window or aperture is the round window of the cochlea, said tube end being adapted to penetrate said round window and said sealing material is arranged to conform with said tube end and said round window to seal said intersection therebetween.

14. An acoustical transmission means as defined in claim 13 wherein said bore at said tube end is open and said gel or paste does not adversely affect in any biological manner the characteristics of the perilymph in the cochlea and wherein said gel or paste maintains its form without penetrating substantially into the perilymph over time.

15. An acoustical transmission means as defined in claim 10 wherein said window or aperture is the oval window of the cochlea, said tube end being adapted to abut said oval window and said sealing material is arranged to conform with said tube end and said oval window to said said intersection therebetween.

16. An acoustical transmission means as defined in claim 10 wherein said window or aperture is the oval window of the cochlea, said tube end being adapted to penetrate said oval window and said sealing material is arranged to conform with said tube end and said oval window to seal said intersection therebetween.

17. An acoustical transmission means as defined in claim 16 wherein said bore at said tube end is open and said gel or paste does not adversely affect in any biological manner the characteristics of the perilymph in the cochlea and wherein said gel or paste maintains its form without penetrating substantially into the perilymph over time.

18. An acoustical transmission means as defined in claim 10 wherein said window or aperture is an aperture opened in the cochlea by surgical fenestration leaving a lining thereacross, said tube end being adapted to abut said lining and said sealing material is arranged to conform with said tube end and said aperture to seal seal intersection therebetween.

19. An acoustical transmission means as defined in claim 10 wherein said window or aperture is an aperture opened in the cochlea by surgical fenestration leaving a lining thereacross, said tube end being adapted to penetrate said lining and said sealing material is arranged to conform with said tube end and said aperture to seal said intersection therebetween.

20. An acoustical transmission means as defined in claim 19 wherein said bore at said tube end is open and said gel or paste does not adversely affect in any biological manner the characteristics of the perilymph in the cochlea and wherein said gel or paste maintains its form without penetrating substantially into the perilymph over time.

21. A hearing aid, comprising:
electro-mechanical means for converting acoustical energy to mechanical motion characteristic thereof;
gel or paste transmission means coupled to said electro-mechanical means for conducting said mechanical motion therefrom; and
impedance matching means, terminating said gel or paste transmission means and adapted to be disposed in direct operative association with a window or aperture in the cochlea for introducing said mechanical motion therethrough.

22. A hearing aid as defined in claim 21 wherein said gel or paste transmission means comprises:
a tube defining a bore therethrough and a sound input end coupled to said electro-mechanical means for receiving said mechanical motion therefrom; and
a gel or paste filling said bore.

23. A hearing aid as defined in claim 22 wherein said gel or paste has equivalent acoustical characteristics as the perilymph.

24. A hearing aid as defined in claim 22 wherein said gel or paste maintain its form substantially over time.

25. A hearing aid as defined in claim 22 wherein said gel is silicone gel.

26. A hearing aid as defined in claim 22 wherein said paste is a mixture of powdered silicon dioxide in a silicone liquid.

27. A hearing aid as defined in claim 22 wherein said impedance matching means comprises:
a sound output end defined by said tube wherein said bore therein is substantially circular and has a diameter being adapted to abut with substantially one-half the diameter of said window or aperture which said output end is disposed at an operative intersection therewith; and
means for sealing said intersection.

28. A hearing aid as defined in claim 22 wherein said impedance matching means comprises:
an output end defined by said tube wherein said bore therein is substantially circular and has a diameter being adapted to abut with an area substantially greater than one-half the diameter of said window or aperture which said output end is disposed at an operative intersection therewith; and
means for sealing said intersection.

29. A hearing aid as defined in claim 22 wherein said impedance matching means further comprises a membrane defined by said tube across said tube end.

30. A hearing aid as defined in claim 22 wherein said sealing means comprises a sealing material arranged to seal said intersection.

31. A hearing aid as defined in claim 30 wherein said window or aperture is the round window of the cochlea, said output end being adapted to abut said round window, and said sealing material is arranged to conform with said output end and said round window to seal said intersection therebetween.

32. A hearing aid as defined in claim 30 wherein said window or aperture is the round window of the cochlea, said output end being adapted to penetrate said round window and said sealing material is arranged to conform with said output end and said round window to seal said intersection therebetween.

33. A hearing aid as defined in claim 22 wherein said bore at said tube end is open and said gel or paste does not adversely affect in any biological manner the characteristics of the perilymph in the cochlea and wherein said gel or paste maintain its form without penetrating substantially into the perilymph over time.

34. A hearing aid as defined in claim 30 wherein said window or aperture is the oval window of the cochlea, said output end being adapted to abut said oval window and said sealing material is arranged to conform with said tube end and said oval window to seal said intersection therebetween.

35. A hearing aid as defined in claim 30 wherein said window or aperture is the oval window of the cochlea, said output end being adapted to penetrate said oval window and said sealing material is arranged to conform with said output end and said oval window to seal said intersection therebetween.

36. A hearing aid as defined in claim 35 wherein said bore at said tube end is open and said gel or paste does not adversely affect in any biological manner the characteristics of the perilymph in the cochlea and wherein sad gel or paste maintains its form without penetrating substantially into the perilymph over time.

37. A hearing aid as defined in claim 30 wherein said window or aperture is an aperture opened in the cochlea by surgical fenestration leaving a lining thereacross, said output end being adapted to abut said lining and said sealing material is arranged to conform with said output end and said aperture to seal said intersection therebetween.

38. A hearing aid as defined in claim 30 wherein said window or aperture is an aperture opened in the cochlea by surgical fenestration leaving a lining thereacross, said output end being adapted to penetrate said lining and said sealing material is arranged to conform with said output end and said aperture to seal said intersection therebetween.

39. A hearing aid as defined in claim 38 wherein said bore at said output end is open and said gel or paste does not adversely affect in any biological manner the characteristics of the perilymph in the cochlea and wherein said gel or paste maintains its form without penetrating substantially into the perilymph over time.

40. A hearing aid as defined in claim 21 wherein said hearing aid is encased in biologically inert material for implanting adjacent the hearing system.

41. A hearing aid as defined in claim 21 wherein said electro-mechanical means comprises microphone means for receiving said acoustical energy and converting said energy into electrical signals characteristic thereof.

42. A hearing aid as defined in claim 41 wherein said electro-mechanical means further comprises:
amplifier means for amplifying said electrical signals into amplified signals;
transducer means for converting said amplified signals into mechanical motion characteristic thereof; and
battery power means for energizing said hearing aid.

43. A method for improving the hearing of a hearing impaired subject, said method comprising the steps of:
surgically interposing a gel or paste transmission means from a proximal end thereof to a distal end thereof in operative association with a window or aperture in the cochlea of the subject;
converting acoustical energy external to the subject into mechanical motion characteristic thereof; and
applying the mechanical motion to the proximal end of the gel or paste transmission means.

44. A method as defined in claim 43 wherein said surgically interposing step includes sealably penetrating said window or aperture with said distal end.

45. A method as defined in claim 43 wherein said surgically interposing step includes abutting said distal end against said window or aperture.

46. A method as defined in claim 43 wherein said surgically interposing step includes spacing said distal end outside said window or aperture and mechanically connecting said distal end to said window or aperture with a plug.

47. A method as defined in claim 43 wherein said surgically interposing step includes cutting an aperture in the vestibule or promontory of the cochlea.

48. A method as defined in claim 43 wherein said method further comprises:
implanting an electro-mechanical amplification means in the mastoid bone of the subject; and,
said surgically interposing step includes operatively associating said proximal end of said gel or paste transmission means with said electro-mechanical amplification means.

* * * * *